United States Patent [19]
Schuman

[11] Patent Number: 5,944,713
[45] Date of Patent: Aug. 31, 1999

[54] METHOD OF TREATING A BODY CAVITY USING AN ENDOSCOPIC SURGICAL LASER

[75] Inventor: Daniel Schuman, Boca Raton, Fla.

[73] Assignee: Surgical Laser Technologies, Inc., Montgomeryville, Pa.

[21] Appl. No.: 08/925,878

[22] Filed: Sep. 9, 1997

Related U.S. Application Data

[63] Continuation of application No. 08/413,281, Mar. 30, 1995, which is a continuation of application No. 08/123,697, Sep. 17, 1993, abandoned, which is a continuation of application No. 07/841,053, Feb. 25, 1992, abandoned.

[51] Int. Cl.$^6$ .................................................. A61N 5/06
[52] U.S. Cl. .................................. 606/10; 606/2; 606/15; 606/27; 607/96; 607/100; 607/105
[58] Field of Search .............................. 606/2, 3–19, 27; 600/108; 607/96, 100–105

[56] References Cited

U.S. PATENT DOCUMENTS

| | | |
|---|---|---|
| 3,982,541 | 9/1976 | L'Esperance, Jr. . |
| 4,146,019 | 3/1979 | Bass et al. . |
| 4,207,874 | 6/1980 | Choy . |
| 4,313,431 | 2/1982 | Frank . |
| 4,408,598 | 10/1983 | Ueda . |
| 4,418,688 | 12/1983 | Loeb . |
| 4,419,987 | 12/1983 | Ogiu . |
| 4,445,517 | 5/1984 | Feild . |
| 4,557,255 | 12/1985 | Goodman . |
| 4,566,437 | 1/1986 | Yamaguchi . |
| 4,572,163 | 2/1986 | Collins et al. . |
| 4,592,353 | 6/1986 | Daikuzono . |
| 4,606,330 | 8/1986 | Bonnet . |
| 4,617,915 | 10/1986 | Arakawa . |
| 4,736,743 | 4/1988 | Daikuzono . |
| 4,770,653 | 9/1988 | Shturman . |
| 4,850,351 | 7/1989 | Herman et al. . |
| 4,881,523 | 11/1989 | Heckele . |
| 4,950,267 | 8/1990 | Ishihara et al. ........................... 606/13 |
| 5,071,422 | 12/1991 | Watson et al. . |
| 5,154,166 | 10/1992 | Chikama . |
| 5,169,396 | 12/1992 | Dowlatshahi et al. .................... 606/14 |
| 5,222,953 | 6/1993 | Dowlatshahi ................................ 606/7 |

FOREIGN PATENT DOCUMENTS 2 147 209  5/1985  United Kingdom .

*Primary Examiner*—David M. Shay
*Attorney, Agent, or Firm*—Seidel, Gonda, Lavorgna & Monaco, PC

[57] ABSTRACT

A method of treating the interior surface of a body cavity of a patient using an optical fiber having at its distal end a tip which partially absorbs and partially emits laser radiation supplied to the tip by the optical fiber. The distal end of the optical fiber is inserted into the cavity. An irrigating fluid is introduced into the cavity, wherein the fluid irrigates the interior surface. The irrigating fluid is in heat-transfer relationship with the tip. The irrigation fluid is heated by supplying laser radiation to the tip whereby laser radiation absorbed by the tip raises the temperature of the tip and the surrounding irrigating fluid. The surface of the body cavity to be treated is selectably exposed with the laser radiation for thermally and optically treating said surface.

16 Claims, 6 Drawing Sheets

METHOD OF TREATING A BODY CAVITY USING AN ENDOSCOPIC SURGICAL LASER

This is a continuation of application(s) Ser. No. 08/413,281 filed on Mar. 30, 1995 which is a continuation of Ser. No. 08/123,697 filed on Sep. 17, 1993, now abandoned, which is a continuation of Ser. No. 07/841,053 filed on Feb. 25, 1992, now abandoned.

FIELD OF THE INVENTION

This invention pertains to a method of treating a body cavity of a patient, and more particularly to a method using a laser and irrigating fluid for treating a body cavity such as a sinus.

BACKGROUND OF THE INVENTION

Endoscopic tools are presently used in certain types of surgery including sinus surgery. In use, the surgeon inserts an endoscope into the sinus of a patient in order to view the microscopic operating field with an optical, electronic viewing system. That opto-electronic system includes an optical sensor positioned at a distal end of a stem of an endoscope. The image captured by the optical sensor is optically and electronically transmitted, enhanced by electronics, and viewed by the surgeon on a monitor.

One type of endoscope has an elongated, hollow stem, an enclosure at a proximal end of the stem opposite the distal end of the stem and a camera port extending opposite the stem from the enclosure. On the top side of the enclosure, finger holes or a finger ring is provided to receive the surgeon's fingers. At the bottom of the enclosure is a stiff spring control valve interface, configured as a depressible valve control, which controls the flow of an irrigating fluid injected through the stem and out of the distal end of the stem. Irrigation is provided via an irrigation port in the enclosure. The endoscope includes continuous suction flow through the stem from the distal end and out a suction port disposed in the enclosure. The irrigation port and the suction port are fluidly coupled to the stem within the enclosure.

Endoscopic surgery using this type of endoscope is sometimes used to clear and remove polyps and growths and debris from the sinus cavities of a patient. A laser delivery system may be inserted into the sinus to burn away the polyps or other nasal obstructions using laser radiation. However, increased bleeding associated with the removal of polyps is frequently a limiting factor in the ability to widely remove diseased tissue.

It is desired to have a method of removing polyps or other nasal obstructions using a laser wherein the excess bleeding typically associated with sinus surgery is reduced.

SUMMARY OF THE INVENTION

This invention relates to a method of treating a body cavity of a patient. An optical fiber having at its distal end a tip, is inserted into the cavity. Laser energy is supplied to the tip by the optical fiber. An irrigating fluid is introduced into the cavity, to irrigate the body cavity. The irrigating fluid is in heat-transfer relationship with the tip, and is heated by supplying laser energy to the tip whereby laser energy is converted into thermal energy by the tip and raises the temperature of the tip and the surrounding irrigating fluid.

In a preferred embodiment, the laser tip is partially transmissive and partially absorptive and the body cavity to be treated is selectably exposed to the laser radiation for thermally and optically treating said body cavity.

In a preferred embodiment, the surface of the body cavity which is mucocutaneous, such as a sinus cavity, is treated and the heating of the irrigating fluid results in heating of the surface tissue, and consequently vasoconstriction of the tissue. Thus, the heating constricts the blood vessels, which results in reduced bleeding when surface tissue is removed.

Other objects, aspects, and advantages of the present invention will be apparent to those skilled in the art upon reading the specification, drawings, and claims which follow.

BRIEF DESCRIPTION OF THE DRAWINGS

Further objects and advantages of the present invention can be found in the detailed description of the preferred embodiment when taken in conjunction with the accompanying drawings in which.

DETAILED DESCRIPTION OF THE PREFERRED EMBODIMENTS

The Surgical Tool

Figure 1:
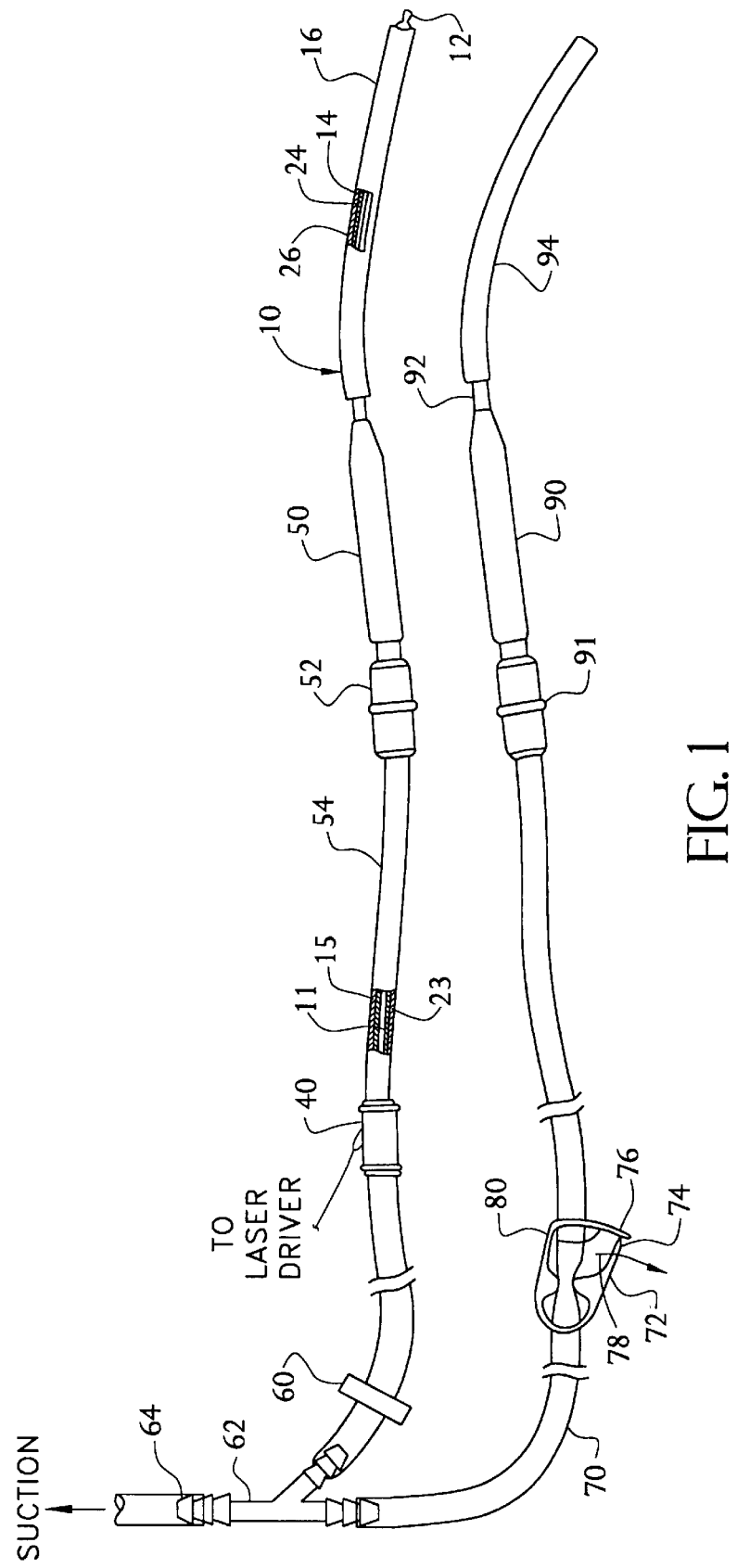
FIG. 1 illustrates an endoscopic surgical tool in accordance with the principles of the present invention and which is used in combination with a laser and a laser power tube.

Referring to the drawings, where like elements are identified by like numerals, there is shown in FIG. 1 a laser delivery portion of an endoscopic surgical tool 10 that can be used in a preferred embodiment of the inventive method of treating the interior surface of a body cavity of a patient.

In endoscopic surgery of the sinuses, the surgeon treats diseased mucosa and polyps in both the nasal passages and sinuses. The desire is to selectively weaken the diseased tissues, thereby causing them to separate from healthy tissue and be easily removed with little bleeding and trauma to the surrounding structures.

Referring to FIG. 1, the surgical tool 10 has a branch coupler 62 connecting a coupling tube 54 and a secondary coupling tube 70. The primary coupling tube 54 contains a portion of a laser delivery system 11. The laser delivery system 11 has a laser tip 12 detachably connected to a laser power tube 14. The laser tip 12 is at least partially absorptive.

Figure 5:
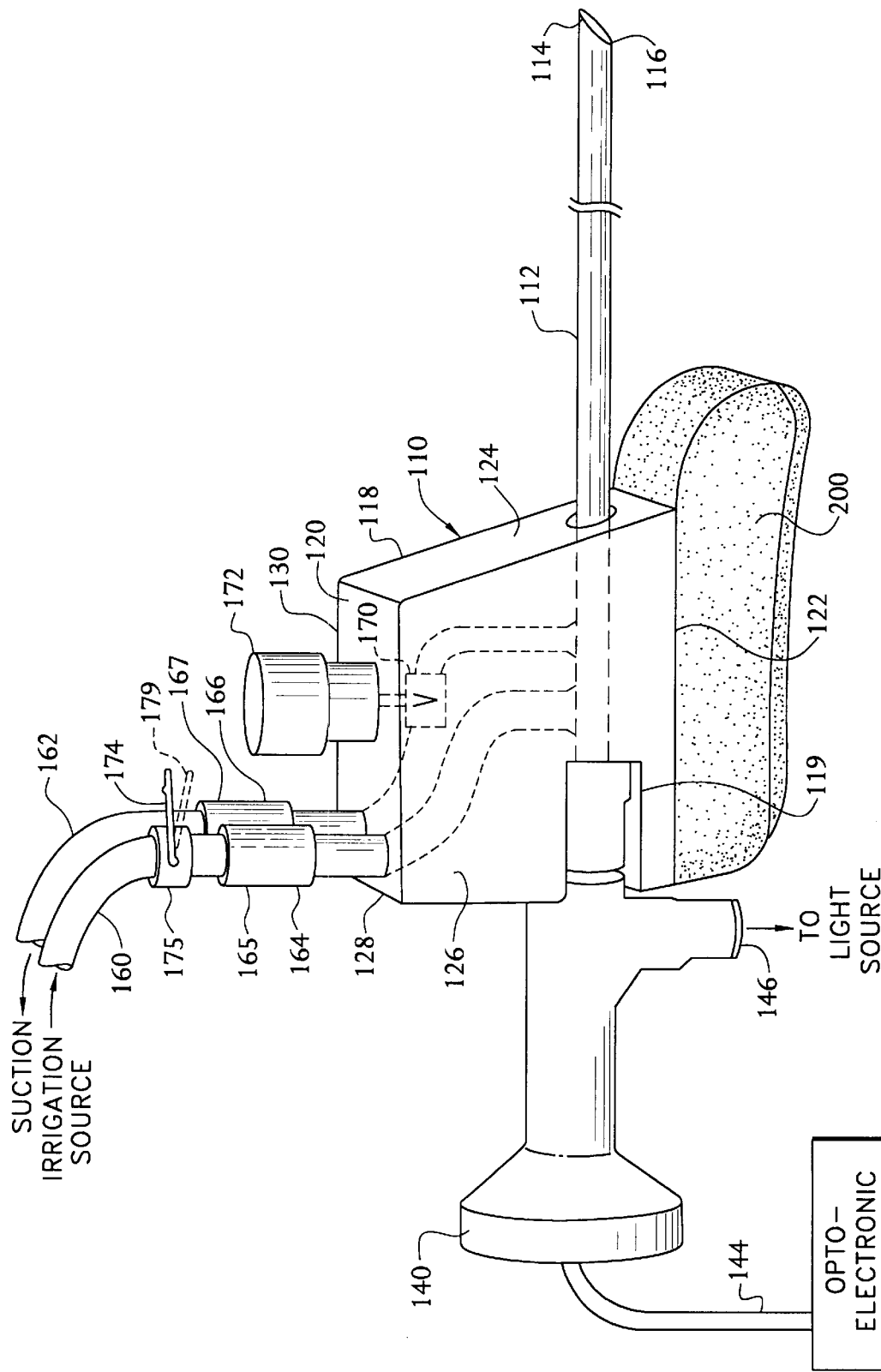
FIG. 5 illustrates an endoscope having a form-fitted palm rest and operator interface controls for suction and irrigation valves wherein the interface controls are configured as a trumpet-like control system.

The surgical tool 10 that contains the laser delivery system 11 is shown separately from an endoscope 110 shown in FIG. 5. It is recognized that a single endoscope could contain the laser delivery system 11, and means for viewing endoscopic surgery, providing additional suction from an operating field and for irrigating the field. The surgical tool 10 and the endoscope 11 are shown separately for purpose of discussion and not to imply that the separate tool is preferable over a single tool.

Figure 2:
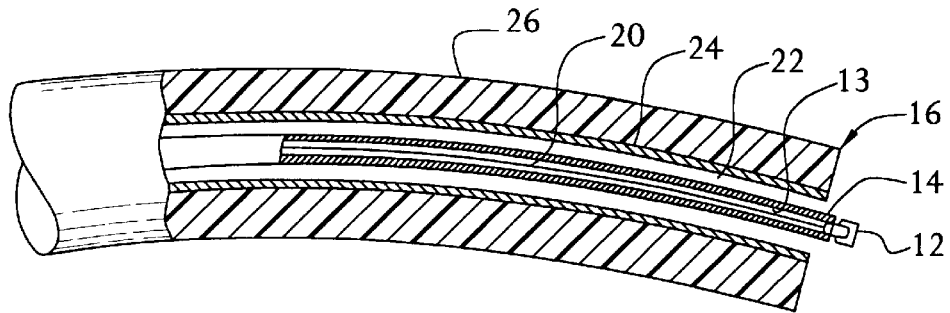
FIG. 2 illustrates an enlarged, cross-sectional view of the distal end of the rigid, bendable tube loosely retaining the laser power tube therein and which illustrates the laser tip protruding from the distal end thereof.

Referring back to FIG. 1, the laser tip 12 is screwed onto the laser power tube 14 at a distal end 16 of the tool 10. FIG. 2 is an enlarged, cross-sectional view of the distal end 16 of the surgical tool 10. A laser feed, commonly referred to as fiber optics, 20 is located in a lumen 13 of the laser power tube 14. An irrigating fluid 18 flows through the lumen 13 of the laser power tube 14 in order to irrigate the operating field, such as a sinus 28 shown in FIG. 7A. This fluid exits from the laser power tube 14 slightly behind the laser tip 12.

In a preferred embodiment, the outside casing of the laser power tube 14 is made of a plastic or polymer. Preferably, laser power tube 14 is energized by an Nd:YAG laser, such as Model CL MD 110/40, manufactured by Surgical Laser Technologies, Inc. It will be recognized by those skilled in the art that other wavelengths can be used.

The laser power tube 14 is loosely disposed or retained in a lumen 22 of a bendable, rigid tube 24. An axially movable, soft-touch casing 26 surrounds the bendable tube 24. The soft-touch casing 26 extends over substantially all of the bendable tube 24. The soft-touch casing 26 enables the surgeon to insert this surgical tool into the body cavity without damaging the surrounding tissue.

Fluid and debris from inside a body cavity are suctioned via the lumen 22 of the bendable tube 24 from the operating field located at a distal end 25 of the bendable tube 24. Irrigating fluid 18 flows through the lumen 13 of the laser power tube 14 into the operating field, and the fluid and debris are suctioned via the lumen 22 of the bendable tube 24.

In a preferred embodiment, the bendable, rigid tube 24 is made of metal. Since the tip laser actually becomes hot and since the bendable metal tube 24 conducts heat, the soft-touch casing 26 is made of a soft, resilient, rubber-like or insulative plastic to limit the conduction of heat to the surrounding tissue.

Since blood vessels may be sized up to 2 millimeters in diameter, the size of the endoscopic tools used in microscopic laser surgery is important. The laser power tube 14 has a 2 millimeter diameter whereas the laser power core 20 has a 0.6 millimeter diameter. The laser tip 12 has substantially the same diameter as the laser power tube 14. In a preferred embodiment, the tip 12 of the laser is coated such that the tip is partially transmissive and partially absorptive.

In a preferred embodiment, the lumen 22 is approximately 3.5 millimeters in diameter. The bendable metal tube 24 is approximately 14 centimeters in length and the soft-touch, axially movable casing 26 is approximately 12.5 centimeters in length.

The distal end 16 of the primary coupling tube 54 has been discussed in detail. In addition, still referring to FIG. 1, the primary coupling tube 54 of the surgical tool 10 has a proximal lumen region 23 and a proximal laser power tube portion 15. At its proximal end, the bendable tube 24 is surrounded by a handle 50. The bendable tube 24 extends through the handle but the handle portion of the tube is not bendable. The handle 50 also includes a hole linking the lumen of the bendable tube 24 with the ambient environment. By closing the hole, the surgeon increases the degree of suction at the end 25 of the bendable tube 24. By opening the hole to the ambient environment, the degree of suction at the distal end of the tube is decreased since air is suctioned through the hole in the handle. The base of the handle 50 is attached to the irrigation coupling tube 54 with a coupler 52.

The surgical tool 10 has a laser power tube insertion port 40 located in the proximal region. The insertion port 40 is positioned in the coupling tube 54 and permits insertion of the laser power tube 14 into the lumen of the coupling tube 54 as well as the lumen 22 of the bendable tube 24. Conventionally, the laser power tube 14 is coupled to a laser and a source of irrigating fluid. The insertion port 40 is fluidly sealed to limit leakage of fluid and debris passing through the coupling tube 54 due to the suction therethrough. The insertion port 40 may be pneumatically sealed to provide good suction control through the tubes 54 and 24.

Still referring to FIG. 1, a suction control valve 60 is disposed on the coupling tube 54. Beyond control valve 60 the branch coupler 62 is attached to the tube 54. A suction pump or other suitable suction source is coupled to one port 64 of branch coupler 62. The branch coupler 62 provides suction for the primary coupling tube 54 and the secondary coupling tube 70.

The secondary coupling tube 70 is connected to the second branch of the branch coupler 62. A flow control device 72 is disposed on the secondary coupling tube 70. In a preferred embodiment, the flow control device 72 is a plastic crimp controller which, upon depression of a lever or catch arm 74, pinches the coupling tube 70 thereby preventing suction and flow of fluid and debris through that tube. When a spring loaded arm 76 is moved away from the catch arm 74, the catch arm 74 moves outboard or away from the tube pinch point as shown by arrow 78 and suction is permitted through the coupling tube 70. Upon depression of the operating lever catch arm 74 in a direction opposite arrow 78, the control valve 72 pinches the coupling tube 70 while the lever catch arm 74 locks into one of a plurality of catch ridges on the inboard side 80 of the arm 76.

The secondary coupling tube 70 is removably connected to a handle 90, via the detachable coupler 91, and ultimately to a bendable, rigid metal tube 92 having a soft-touch casing 94 surrounding a substantial portion thereof and particularly the distal end of the metal tube. The secondary bendable, rigid tube 92 and casing 94 is substantially the same as the primary tube 24 except that the primary tube loosely retains the laser power tube therein. The soft casing on the tube 92 may be axially moved to expose or cover the distal end of the tube 92. Other tools can be attached to the tube 70 via the detachable coupler 91 by removal of the handle 90 therefrom.

Figure 4:
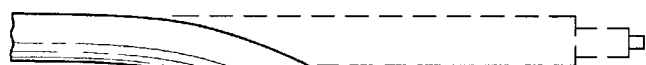
FIG. 4 diagrammatically illustrates the distal end of the rigid tube with a soft-touch casing axially moved to expose the end of the rigid tube and which further illustrates how the rigid tube can be bent.

Referring back to the primary coupling tube 54 as shown in FIG. 4, the distal end 16 of the surgical tool 10 can be bent by the surgeon such that the tube, as well as the loosely retained laser tip and laser power tube, can be placed at specific locations in the body cavity of a patient during the microscopic, endoscopic surgery. The soft-touch casing 26 can be axially moved to expose the end 25 of the bendable tube 24.

Figure 3:
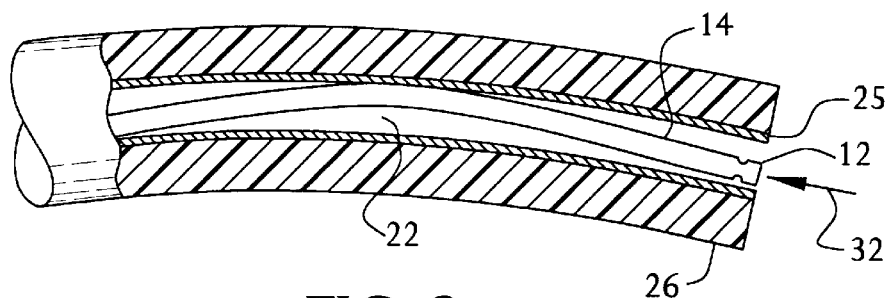
FIG. 3 illustrates an enlarged, cross-sectional view of the distal end of the rigid, bendable tube as shown in FIG. 2, wherein the laser power tube is axially compressed within the rigid, bendable tube.

Referring to FIG. 3, the tube end 25 of the bendable tube 24 is covered by the casing 26 thereby substantially eliminating a sharp tube end which may present a problem during microscopic, endoscopic surgical procedures. Alternatively, the distal end region 30 of the tip laser 12 and laser tube 14 protrudes from the bendable tube 24 as shown in FIG. 4. The dashed lines in FIG. 4 represent the distal end region 16 being straightened as compared with the curved distal end region 16 shown in solid lines. FIG. 3 shows that the laser power tube 14 and hence the laser tip 12 can move axially within the lumen 22 upon application of an axially aligned inboard directed force shown by arrow 32.

The endoscope 110 is primarily used in conjunction with the surgical tool 10 for viewing endoscopic surgery, providing additional suction from the operating field, and for irrigating the field. Additionally, the scope provides continuously variable suction and controlled irrigation to the microscopic operating field. As stated above, it is recognized that the laser delivery system can be separate and used in combination with an endoscope 110 as shown in FIG. 5, or an endoscope can combine all the features.

Referring to FIG. 5, the endoscope 110 has an elongated, hollow stem 112 (sometimes called a sheath) and the stem has a lumen 114 and a distal end 116. At its proximal end, the stem 112 is rotatably connected to a handle enclosure 118. The handle enclosure 118 includes a top 120, a bottom 122, and four adjoining sides 124, 126, 128, and 130. Extending from the back side 128 of the enclosure 118 is an end 139, which includes a camera port 140. The camera port 140 may be part of the stem. The enclosure 118 has a side view port 119 that permits the surgeon to visually confirm and mechanically change the rotative position of the stem 112 with respect to the handle enclosure 118. The camera port 140 is sometimes referred to as a camera ring. The port 140 permits 360° rotation for the optoelectronic cables attached thereto. An optical electronic viewing system 142 is optically and/or electronically connected to the camera port 140 via a coupler line 144. A light source port 146 is adapted to be coupled to a light source. A telescope (not shown) is loosely inserted into the lumen 114 of the stem 112. As the surgeon rotates the entire end 139 of the scope, the field of view rotates.

The endoscope 110 includes a pair of coupling hoses 160 and 162 that are coupled to an irrigation source and a suction device respectively. Accordingly, the endoscope 110 includes a irrigation port 164 and a suction port 166. These ports may be configured with removable coupling attachments 165 and 167 which enable coupling hoses 160 and 162 to be removably attached and fluidly sealed to the endoscope 110. The irrigation and suction ports 164 and 166 are fluidly coupled to the lumen of the stem 112, as shown by dashed lines. In laser endoscopic sinus surgery, it is desirable to provide continuous irrigation via the irrigation coupling tube 160 and the stem 112 into the body cavity. On the other hand, it is desirable to provide controlled or variable suction through the suction valve 170 and the operator control interface 172 from the operating field. The flow of irrigation through the irrigation coupler 160 is controlled by the operator control interface 174. Continuous irrigation is desirable in order to flood the surgical field with the irrigating fluid 18 while using the surgical tool 10 shown in FIGS. 1–4.

The fingers of the surgeon operate the trumpet-like controls by depressing the suction interface control 172. The valve 170, controlling the suction, may be biased in a closed position and the operator interface control 172 may be biased upward such that the surgeon must continually depress the interface control 172 to provide the degree of suction from the surgical field via the lumen 114.

Irrigation flow is controlled by the irrigation control valve 175. The operator interface control 174 controls the flow of irrigation through the lumen 114 of the stem 112. The surgeon can adjust the control lever 174 as shown in its dashed position 179 and thereby control the rate of flow into the operating field. This is a set-type or static control. Once the irrigation control valve is set to a certain position by the surgeon, a constant, predetermined flow of fluid is fed to the operating field via the lumen 114. The surgeon need not continually depress the irrigation control valve 175 in contrast to the suction control valve. Also, the control lever is configured as a trumpet-like control which is operated by the surgeon from the top 120 of the enclosure 118.

Figure 6:
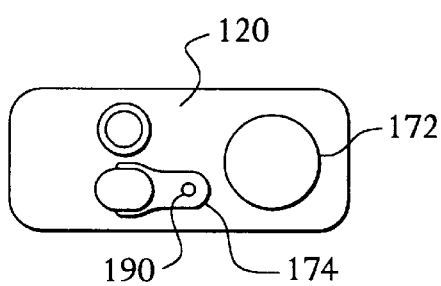
FIG. 6 diagrammatically illustrates a top view of the trumpet-like control system for the endoscope illustrated in FIG. 5.

FIG. 6 shows the operator control interface 174 having a tactile sensor or bump 190 such that the surgeon can sense the irrigation flow lever by touch. The top of the suction control 172 is generally flat with rounded edges because the surgeon is continuously depressing the valve. Suction is primarily controlled by the operator interface 172 since the valve 170 is a variable type control which is preferably biased closed.

The Method of Treating the Interior Surface of a Body Cavity

The method will be described with primary reference to the surgical tool 10. However, it is recognized that the surgeon needs a method of viewing what is taking place at the distal end of the surgical tool, as described above in relation to the endoscope 110. Furthermore, the endoscope 110 can provide additional means for suction from the operating field and for irrigating the field.

Figure 7A:
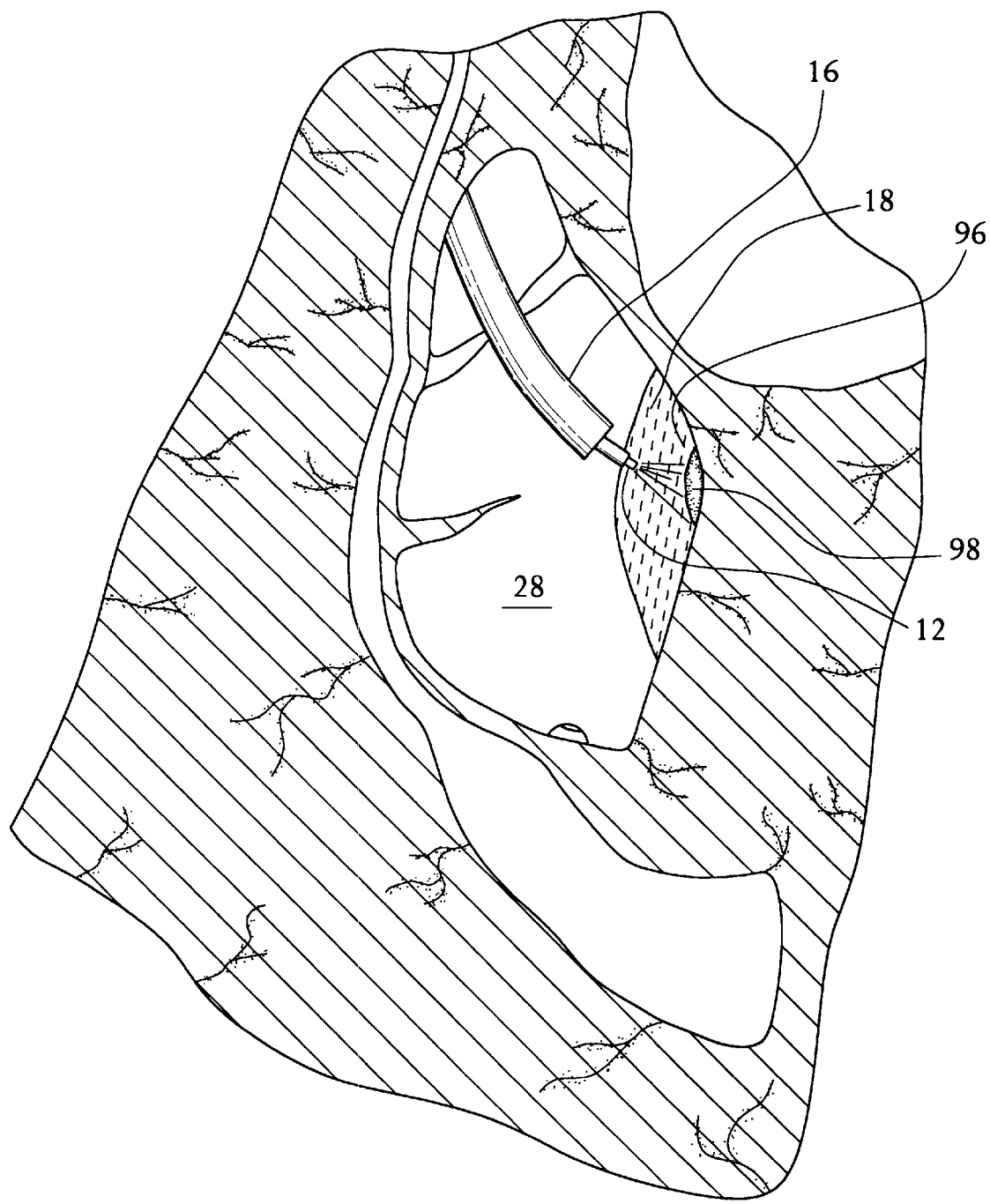
FIG. 7A diagrammatically illustrates treatment of a sinus cavity surgical site with a laser according to the method of the invention.

Referring to FIG. 7A, the distal end 16 of the surgical tool 10 can be bent by the surgeon such that the tube 24, as well as the axially-movable laser tip and laser power tube 14, can be placed at specific locations in the body cavity of a patient, such as a sinus 28, during microscopic endoscopic surgery.

Continuous irrigation is provided to the body cavity, such as the sinus 28, via the irrigation coupling tube 160 and stem 112 of the endoscope 110 or via the lumen of the laser power tube 14 of the surgical tool 10. The irrigating fluid 18 is typically a saline solution which is warmed (not heated) prior to introduction into the surgical tool 10 or the endoscope 110. The irrigating fluid 18 irrigates the surface of the sinus 28.

With the microscopic surgical field (i.e., the sinus) irrigated, the irrigating fluid 18, is heated by the laser tip. Because the tip is at least partially absorptive, the laser radiation absorbed by the tip raises the temperature of the tip and the surrounding irrigating fluid 18. The heated irrigating fluid 18 is localized near the laser tip 12, wherein the surgeon can selectively sear or blanch the sinus tissue in the surgery area 96, including a polyp 98. The heat helps cause the unhealthy tissue to weaken, as through protein denaturation or coagulation. The irrigating fluid 18 dissipates the heat quickly, such that the heat does not materially damage the surrounding healthy tissue.

Furthermore many internal tissues, such as mucocutaneous tissue (e.g., sinuses), the heat causes vasoconstriction of the tissue. This is different from skin which, upon heating, would vasodilate. Thus, the temperature of the irrigation fluid will be selected so as to enhance vasoconstriction.

Figure 7B:
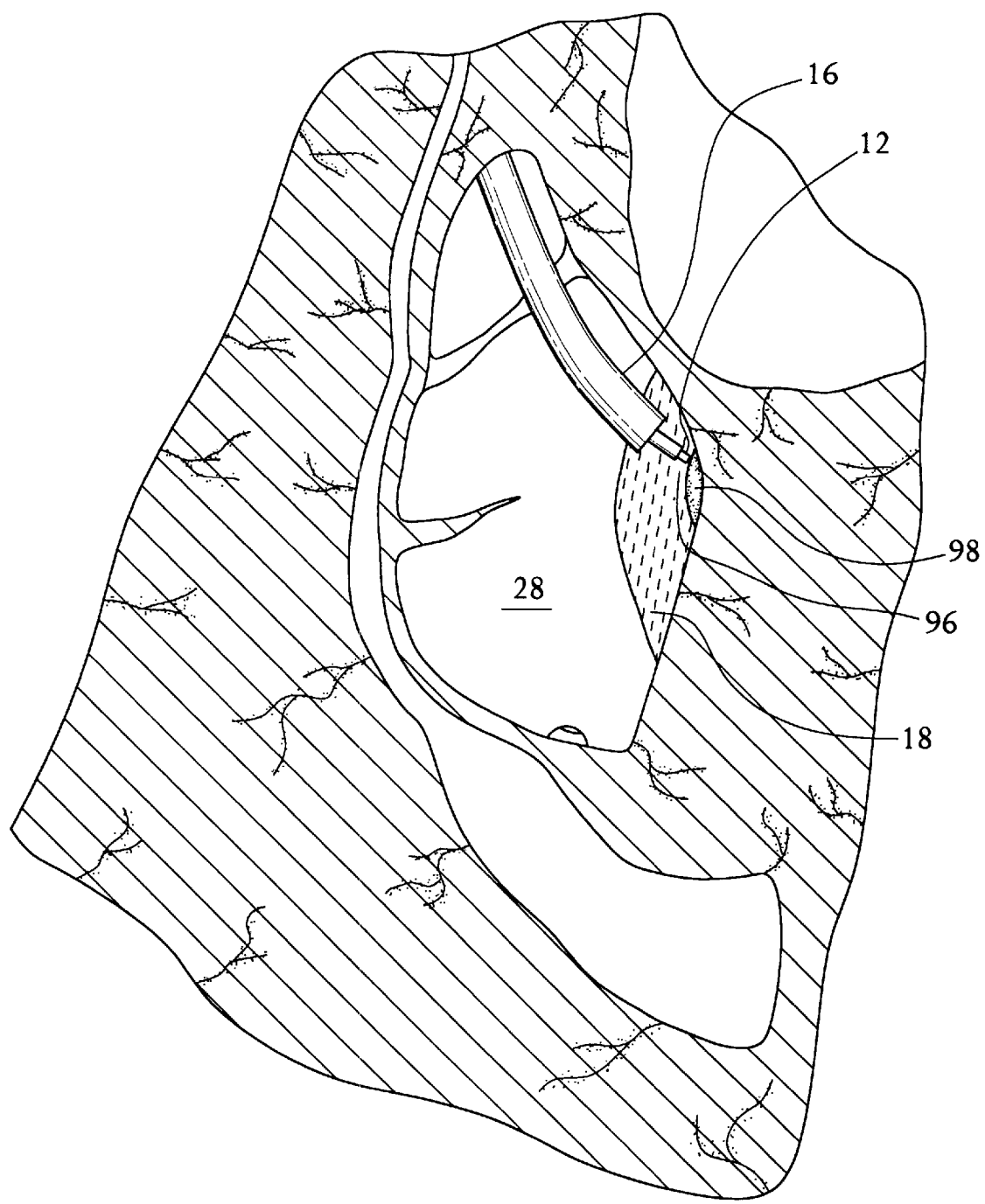
FIG. 7B diagrammatically illustrates contact of a laser tip with tissue of a sinus cavity surgical site with a laser according to the method of the invention.

Referring to FIG. 7B, the flow of the irrigating fluid 18 assists in the peeling away of the polyp 98 by peeling base tissue in layers, and acts as a controlled gentle lavage to clean debris from the surgery area 96, including the polyp 98.

In addition, the surface of the body cavity to be treated, i.e., the polyp 98 in the sinus 28, can be selectably exposed to laser radiation for thermally and/or optically treating the surface to aid in the removal of the polyp 98. The laser tip 12 is extended outward of the distal end 16 of the lumen 22 of the bendable tube 24 by inserting additional lengths of the power tube 14 into the port 40. The laser tip 12 is placed in proximity to or in contact with the polyp 98 to weaken and remove the polyp 98. Since the laser tip 12 in a preferred embodiment is partially transmissive and partially absorptive, the treatment is partially thermal and partially radiative. With the blood vessels in the tissue surrounding the polyp 98 constricted, bleeding is reduced and visualization is thus improved when surface tissue is peeled off as the polyp 98 is removed.

The tube 14 retracts axially within the tube 24 upon application of an axially directed inboard force at the tip 12. If the tip 12 touches a bone or hard structure in the sinus, the power tube 14 retracts axially and compresses within the lumen 22. FIG. 3 shows the laser power tube 14 and the laser tip 12 axially retracted within the lumen 22 upon application of an axially-aligned inboard directed force shown by arrow 32. Compression of the laser power tube 14 of approximately 3 millimeters has been noted in use of the preferred embodiment. The surgeon is thus able to conduct delicate laser microsurgery on soft tissue without damaging the harder tissue surrounding the object being surgically removed or altered. In addition, the laser tip 12 can be used as a probe for diseased tissue.

If the surgeon desires, the surgeon can mechanically treat the surface in addition to irradiating the tissue by axially moving the soft-touch casing 26 to expose the end 25 of bendable metal tube 24, as shown in FIG. 4. This exposure may enable the surgeon to scrape with the laser tip 12 to assist in the removal of objects from the body cavity as seen in FIG. 7B.

Also as stated earlier, the surgeon uses the locally generated heat from the laser to assist in the removal of objects. During the time the surgeon is using the locally generated heat, the control valve 72 on the secondary coupling tube 70 may be closed thereby eliminating or reducing suction through the secondary surgical tool.

If the surgeon desires to clean the operating field and not use the laser endoscopic tool, the surgeon closes the control valve 60 on the primary tube 54, removes the primary surgical tool (bendable tube 24 and soft-touch casing 26) from the body cavity, inserts the secondary surgical tool (bendable tube 92 and soft-touch casing 94), opens the secondary branch control valve 72, thereby permitting suction through the secondary branch coupling tube 70 as well as the secondary endoscopic surgical tool.

The procedure and method described above for the sinus may be performed under a general endotracheal anesthesia.

Figure 7C:
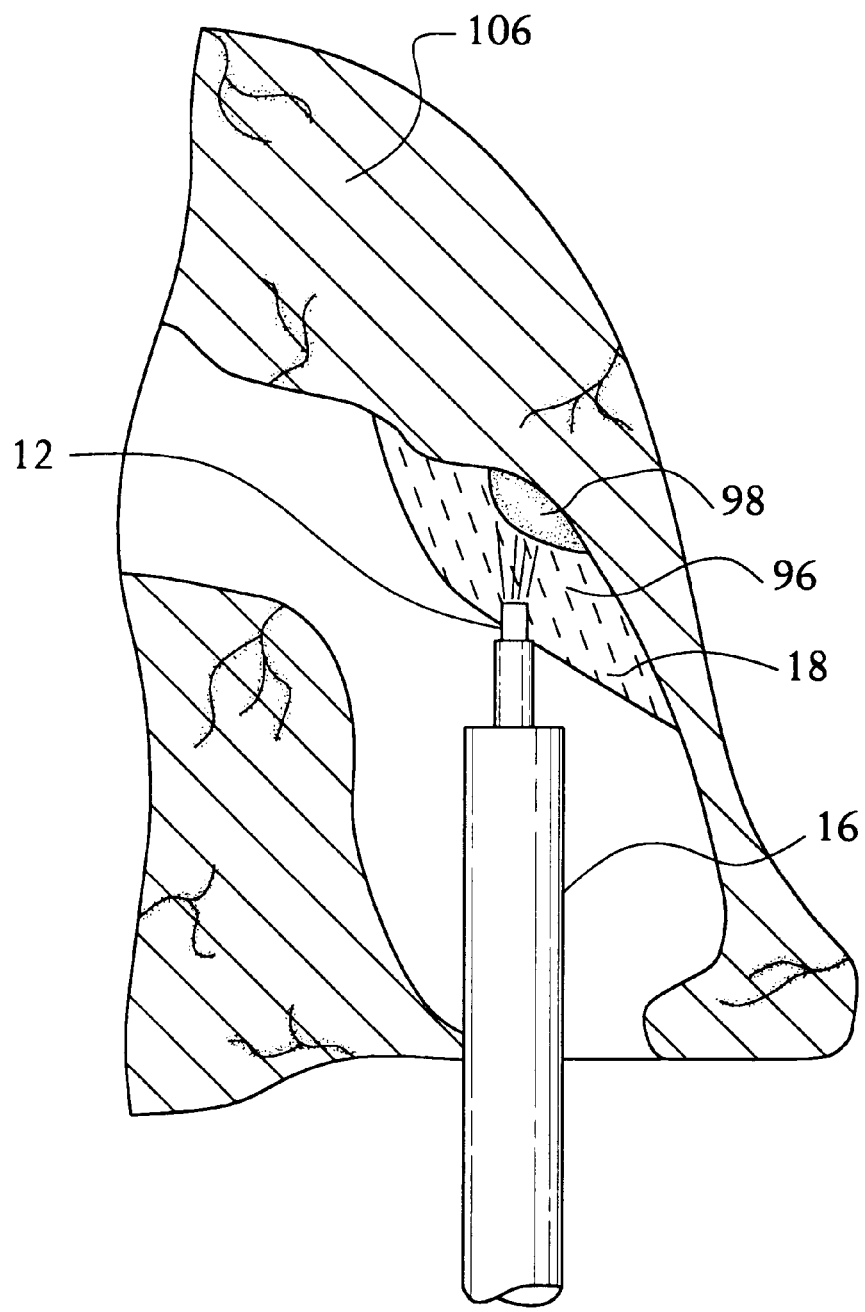
FIG. 7C diagrammatically illustrates treatment of a nose surgical site with a laser according to the method of the invention.

Referring to FIG. 7C, a similar method can be performed in a cavity within a nose 106. The laser radiation absorbed by the tip raises the temperature of the tip and the surrounding irrigating fluid 18. The heated irrigating fluid 18 heats the tissue in the surgery area 96, including a polyp 98, causing coagulation of the polyp and vasoconstriction of the tissue since the nose, similar to the sinus cavity has mucocutaneous tissue. This is in contrast to other tissue in the human body which, upon heating, would vasodilate.

The present invention may be embodied in other specific forms without departing from the spirit or essential attributes thereof and, accordingly, reference should be made to the appended claims, rather than to the foregoing specification, as indicating the scope of the invention.

What is claimed is:

1. A method of treating a body cavity of a patient, comprising the steps of:
    a. inserting an optical fiber into the cavity, the optical fiber having a tip at a distal end of said optical fiber;
    b. supplying laser energy to the tip through the optical fiber;
    c. introducing a heat-transfer fluid into the cavity such that the fluid irrigates the cavity and is in heat transfer relationship with the tip;
    d. converting the laser energy to thermal energy by a coating on the tip;
    e. heating the heat-transfer fluid in proximity to the tip by the thermal energy; and
    f. selectably heating the body cavity by the heated heat-transfer fluid.

2. A method according to claim 1, further comprising the step of selectably exposing said body cavity to be treated with said laser energy for at least one of thermally treating and optically treating said body cavity.

3. A method according to claim 1 further comprising the step of preheating the irrigating fluid prior to introducing it into said body cavity.

4. A method according to claim 1 further comprising contacting said body cavity to be treated with said tip for applying mechanical force to said body cavity for treatment thereof.

5. A method according to claim 1, further comprising the step of selectably contacting tissue of said body cavity directly with said tip for palpating and treating said tissue.

6. A method of treating a body cavity of a patient, comprising the steps of:
    a. inserting into said cavity an optical fiber having a tip at the distal end thereof, laser energy being supplied to said tip by the optical fiber;
    b. introducing into said cavity a heat-transfer fluid and causing said fluid to irrigate said body cavity;
    c. causing the tip to be in heat-transfer relationship to the heat-transfer fluid;
    d. heating said heat-transfer fluid by supplying laser energy to said tip whereby a substantial amount of the laser energy is converted to thermal energy by means formed at the tip for converting laser energy to thermal energy, thereby causing said tip and the heat-transfer fluid in proximity to said tip to become hot; and
    e. selectably heating the body cavity by hot heat-transfer fluid in proximity to said tip for thermally treating said body cavity.

7. A method according to claim 6, further comprising the step of preheating the irrigating fluid prior to introducing it into said body cavity.

8. A method according to claim 6, further comprising contacting said body cavity to be treated with said tip for applying mechanical force to said body cavity for treatment thereof.

9. A method of treating the interior surface of a body cavity of a patient, comprising the steps of:
    a. inserting into said cavity an optical fiber having a tip at the distal end thereof, the tip at least partially absorbing laser radiation supplied to said tip by said optical fiber;
    b. introducing into said cavity a heat-transfer fluid and causing said fluid to irrigate said surface;
    c. causing the tip to be in heat-transfer relationship to the heat-transfer fluid;
    d. heating said heat-transfer fluid by supplying laser radiation to said tip whereby a substantial amount of the laser radiation is absorbed by said tip and converted to thermal energy by means formed at the tip for converting laser radiation to thermal energy, thereby causing said tip and the heat-transfer fluid in proximity to said tip to become hot;

e. selectably heating said surface of said body cavity by the hot heat-transfer fluid in proximity to said tip for thermally treating said surface; and f. selectably contacting tissue of said body cavity directly with said tip for palpating and treating said tissue.

10. A method according to claim 9, further comprising contacting said surface to be treated with said tip for applying mechanical force to said surface for treatment thereof.

11. A method according to claim 9, wherein the body cavity is mucocutaneous, such that the heating of the irrigating fluid results in vasoconstriction of the tissue.

12. A method according to claim 9, wherein the tip partially absorbs and partially emits laser radiation supplied to said tip by said optical fiber.

13. A method according to claim 12, further comprising the step of selectably exposing said surface of said body cavity to be treated with said laser radiation for thermally and optically treating said surface.

14. A method according to claim 13 wherein the tip contacts the surface for the step of selectably exposing said surface of said body cavity to be treated with said laser radiation.

15. A method according to claim 13 wherein the tip is spaced from the surface for the step of selectably exposing said surface of said body cavity to be treated with said laser radiation.

16. A method according to claim 13, further comprising the step of preheating the irrigating fluid prior to introducing it into said cavity.

* * * * *